United States Patent [19]
Dean et al.

[11] Patent Number: 6,028,056
[45] Date of Patent: Feb. 22, 2000

[54] PHARMACEUTICAL COMPOSITIONS FOR IMAGING AND TREATING THROMBI

[75] Inventors: Richard T. Dean; John Lister-James, both of Bedford, N.H.

[73] Assignee: Diatide, Inc., Londonderry, N.H.

[21] Appl. No.: 09/020,086

[22] Filed: Feb. 6, 1998

[51] Int. Cl.[7] .......................... A61K 38/00; A61K 38/16
[52] U.S. Cl. .............................. 514/12; 514/2; 530/323; 530/300
[58] Field of Search ............................... 514/12; 530/323

[56] References Cited

U.S. PATENT DOCUMENTS

| | | | |
|---|---|---|---|
| 5,508,020 | 4/1996 | Dean et al. | 424/1.69 |
| 5,645,815 | 7/1997 | Dean et al. | 424/1.69 |

OTHER PUBLICATIONS

Lister–James, et al., (1994) "A Structure–Activity–Relationship(SAR) Study of GPIIb/IIIa Receptor–Binding Peptides Radiolabeled with Tc–99m for Imaging Thromboembolism" Jnl. of Nucl. Med., 35, 257P (abstract).

Lister–James, et al., (1996) "Thrombus Imaging with a Technetium–99m–Labeled, Activated Platelet Receptor–Binding Peptide" Jnl. Nucl. Med., 37, 775–781.

Muto et al., (1995) "Detecting Deep Venous Thrombosis with Technetium–99m–Labeled Synthetic Peptide P280" Jnl. of Nucl. Med., 36, 1384–1391.

Pearson, et al., (1996) "Thrombus Imaging Using Technetium–99m–Labeled High–Potency GPIIb/IIIa Receptor Antagonists. Chemistry and Initial Biological Studies" Jnl. of Med. Chem., 39, 1372–1382.

Zheng, et al., (1997) "Synthesis and Characterization of 99Tc P246: A Technetium Peptide" American Chemical Society, Division of Inorganic Chemistry, 213th ACS National Meeting, 336.

*Primary Examiner*—Cecilia Tsang
*Assistant Examiner*—Michael Borin
*Attorney, Agent, or Firm*—Patricia A. McDaniels

[57] ABSTRACT

The invention provides novel precursor reagents used in production of imaging agents derived from apcitide. Imaging agents made using the precursor reagents of the invention are useful for in vivo detection and diagnosis of thrombi. The precursor reagents of the invention may also be used in production of antithrombotic agents derived from apcitide.

10 Claims, No Drawings

PHARMACEUTICAL COMPOSITIONS FOR IMAGING AND TREATING THROMBI

The present invention relates to the field of diagnostic imaging of thrombosis. More particularly, the invention relates to pharmaceutical compositions for imaging thrombi. The invention also relates to the field of treatment of thrombosis, using medicaments produced from novel precursor reagents.

BACKGROUND OF THE INVENTION

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths. It has also been estimated that over 90% of all pulmonary emboli arise from DVT in the lower extremities. Anticoagulant therapy can effectively treat these conditions if applied early enough. However, such treatment is associated with risks (e.g. internal bleeding) that prevent unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of localizing thrombi in vivo, most preferably using non-invasive methods, is highly desirable. In the past, contrast venography and compression B-mode ultrasound have been used to identify sites of deep-vein thrombosis; the choice of which technique was used depended on the expected location of the thrombus. However, the former technique is invasive, and both techniques are uncomfortable for the patient. In addition, these methods are in many cases either unsuitable or yield inaccurate results. Current methods used to diagnose PE include chest X-ray, electrocardiogram (EKG), arterial oxygen tension, perfusion and ventilation lung scans, and pulmonary angiography. Apart from the latter (invasive) procedure, none of these methods is capable of providing an unequivocal diagnosis.

Recently, a $^{99m}$Tc-radiolabeled peptide, apcitide, which binds to the GPIIb/IIIa receptor on platelets, a component of thrombi, thereby providing an imaging agent specifically targeted to thrombi, completed clinical trials for scintigraphic imaging of acute DVT. A kit for making $^{99m}$Tc-radiolabeled apcitide, ACUTECT™, is in the process of obtaining approval for sale as a radiopharmaceutical product. ACUTECT™ is formulated with bibapcitide, the chemical structure of which is set forth below.

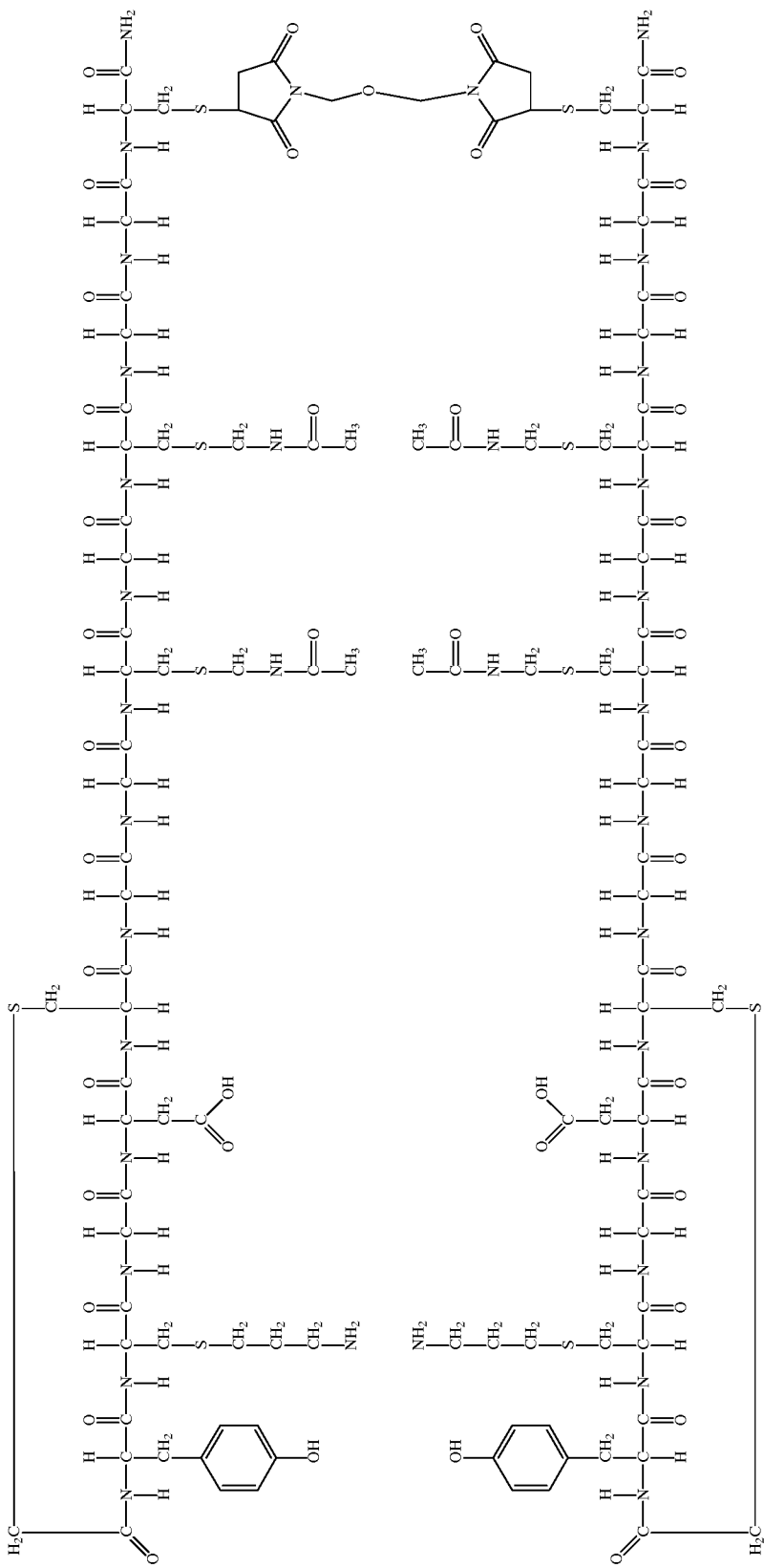

Bibapcitide and radiolabeling thereof are described in commonly assigned U.S. Pat. Nos. 5,508,020 and 5,645,815; in commonly assigned, copending U.S. Ser. No. 08/253,317, now U.S. Pat. No. 5,830,856; and in WO 93/23085; WO 93/25244; WO 94/23758 and WO 95/33496. Commonly assigned WO 94/07918 discloses that bibapcitide may also be used in unlabeled form as an antithrombotic agent.

Bibapcitide is a dimer of the monomer apcitide, which is also disclosed in the above-identified U.S. patents and application and international patent applications. The dimer bibapcitide is formed through a bismaleimide linkage of the carboxy-terminal cysteines of the two apcitide monomers. Monomeric apcitide has been complexed with $^{99}$TcO, and the apcitide/$^{99}$Tc complex has been characterized, in Zheng, et al., Abstract 336, 213th American Chemical Society Meeting, Apr. 13–17, 1997.

SUMMARY OF THE INVENTION

The present inventors have discovered two novel dimers of apcitide, bibapcitide monocarboxylate and bibapcitide dicarboxylate, which are present in aqueous solutions of bibapcitide at pH greater than about 5. These novel apcitide dimers may be employed as precursors for production of $^{99m}$Tc-radiolabeled apcitide.

In one embodiment, the invention provides a precursor reagent comprising bibapcitide monocarboxylate.

In another embodiment, the invention provides a precursor reagent comprising bibapcitide dicarboxylate.

In another embodiment, the invention provides a composition comprising bibapcitide monocarboxylate.

In another embodiment, the invention provides a composition comprising bibapcitide dicarboxylate.

In yet another embodiment, the invention provides a pharmaceutical composition comprising bibapcitide monocarboxylate and a pharmaceutically acceptable carrier.

In another embodiment, the invention provides a pharmaceutical composition comprising bibapcitide dicarboxylate and a pharmaceutically acceptable carrier.

DETAILED DESCRIPTION OF THE INVENTION

The patent and scientific literature referenced herein establish the knowledge available to those with skill in the art. The issued U.S. patents and allowed applications are hereby incorporated by reference.

The pharmaceutical compositions of the invention provide novel precursor reagents, bibapcitide monocarboxylate and bibapcitide dicarboxylate, for producing both imaging agents and antithrombotic agents derived from bibapcitide.

The chemical structure of bibapcitide monocarboxylate is depicted below.

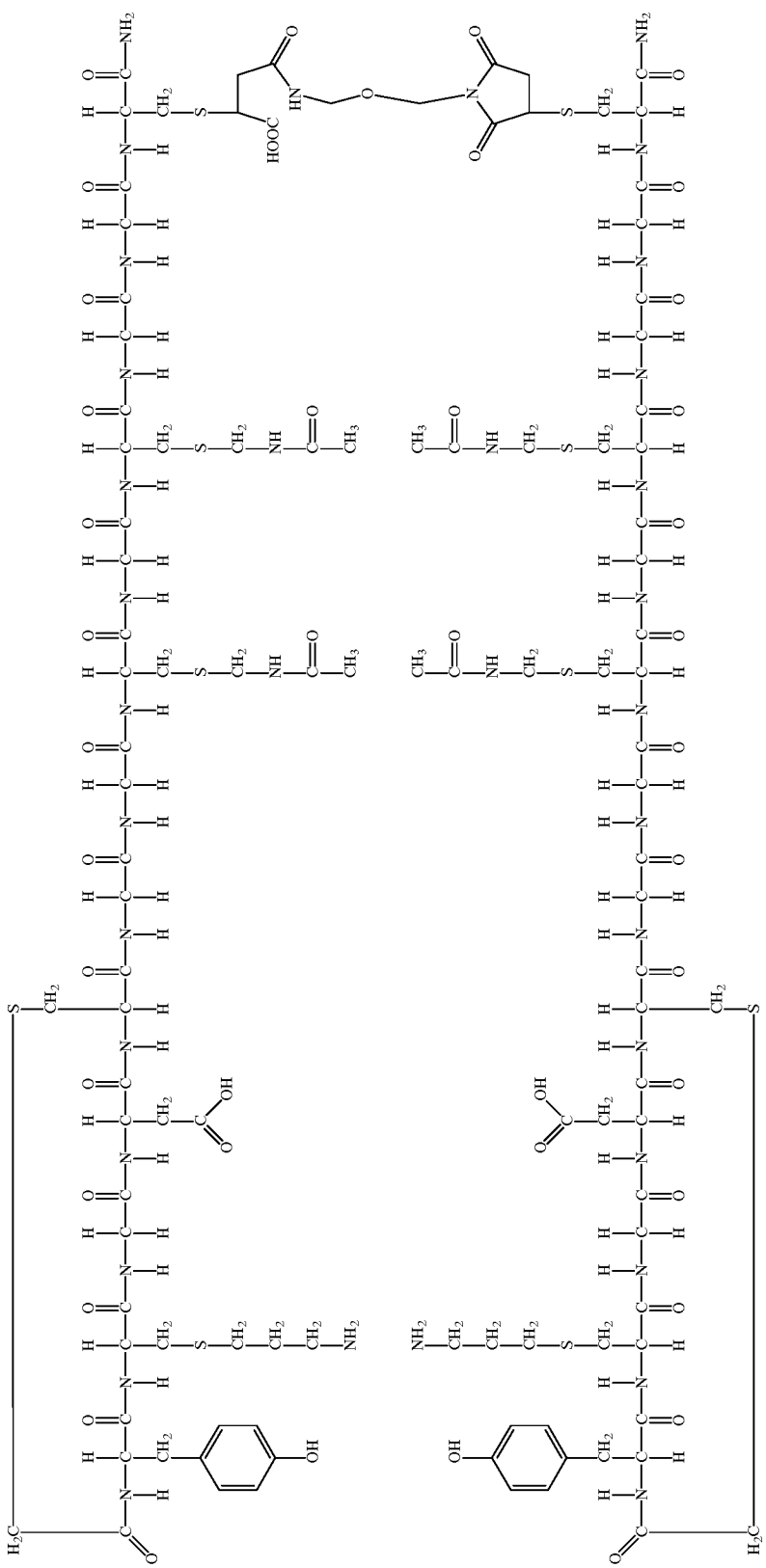

The chemical structure of bibapcitide dicarboxylate is depicted below.

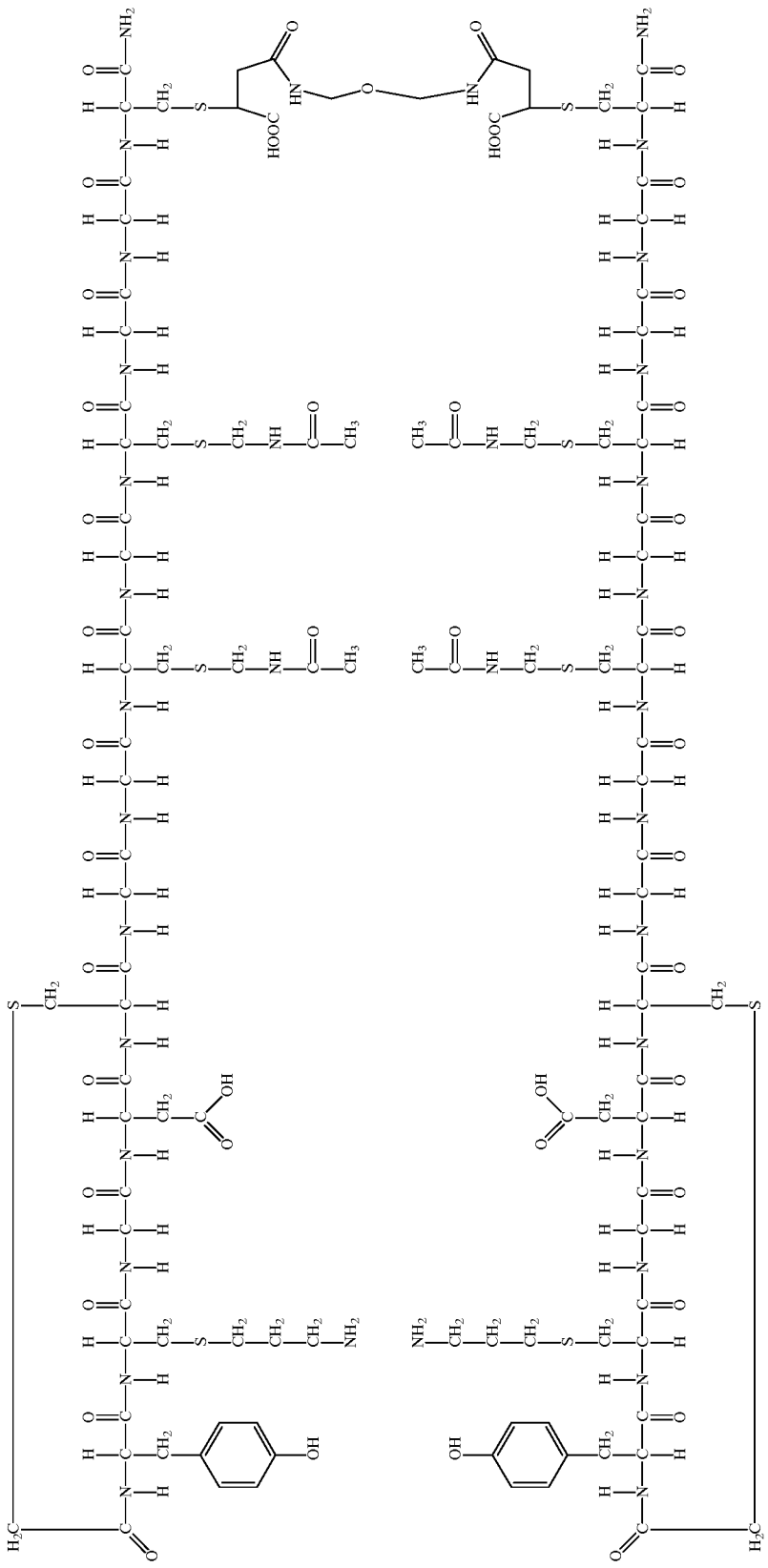

The presence of the free carboxylate groups affords the precursor reagents greater solubility than bibapcitide in aqueous media. For example, a comparison of the solubilities of bibapcitide and bibapcitide dicarboxylate in 0.1 M phosphate buffer at several pH values, at room temperature, is shown in Table 1 below.

TABLE 1

| | Solubilities | |
|---|---|---|
| | Bibapcitide | Bibapcitide-$(COO^-)_2$ |
| pH 7 | <0.05 mg/mL | 1.3 mg/mL |
| pH 8 | <0.05 mg/mL | 1.3 mg/mL |
| pH 9 | <0.05 mg/mL | 1.3 mg/mL |

Bibapcitide is available from Diatide, Inc., Londonderry, N.H., USA. Bibapcitide may be produced, for example, using solid phase peptide synthesis as set forth in U.S. Pat. Nos. 5,508,020; 5,645,815; in U.S. Ser. No. 08/253,317 and in WO 93/23085; WO 93/25244; WO 94/23758; WO 94/07918 and WO 95/33496. Bibapcitide is preferably produced at a pH of less than about 4 and isolated as the trifluoroacetate salt. Bibapcitide trifluoroacetate is solubilized using acetonitrile or ethanol and water or an aqueous solution prior to formulation. For use in mammals such as humans, solubilization with ethanol and water or an aqueous solution is preferred.

Bibapcitide monocarboxylate and bibapcitide dicarboxylate are preferably produced from bibapcitide by raising the pH of the solubilized bibapcitide using a suitable buffer such as a phosphate buffer adjusted to the desired pH, as exemplified in Example 1, or a bicarbonate buffer as disclosed in Example 2. Most preferably, bibapcitide monocarboxylate and bibapcitide dicarboxylate are produced by reconstituting lyophilized bibapcitide trifluoroacetate with a buffer at physiological pH. Any buffer may be used to adjust the pH of the bibapcitide to produce bibapcitide monocarboxylate and/or bibapcitide dicarboxylate. For example, phosphate buffer, bicarbonate buffer, borate buffer, citrate buffer, sulfate buffer, and the like, may be employed to produce the precursor reagents of the invention. Alternatively, bibapcitide monocarboxylate and/or bibapcitide dicarboxylate may be produced enzymatically, for example, using a hydrolase. Bibapcitide monocarboxylate and bibapcitide dicarboxylate may be isolated and purified using known methods, such as HPLC, as shown in Examples 1 and 2.

The stabilities of bibapcitide, bibapcitide monocarboxylate and bibapcitide dicarboxylate at a variety of pH values are set forth in Table 2 below. Stability is expressed in Table 2 in terms of 95% stability time at room temperature.

TABLE 2

| | Stabilities | | |
|---|---|---|---|
| pH | Bibapcitide | Bibapcitide-$(COO^-)$ | Bibapcitide-$(COO^-)_2$ |
| <4 | >5 hours | minutes | minutes |
| 4–5 | 1–5 hours | 1 hour | 1 hour |
| 5–6 | 1 hour | >5 hours | >5 hours |
| 6–7 | minutes | >5 hours | >2 days |
| 7–8 | minutes | 1 hour | >5 hours |
| >8 | minutes | minutes | 1 hour |

The precursor reagents of the invention may be provided in the form of a pharmaceutical composition. Preferably, the pharmaceutical composition of the invention comprises bibapcitide monocarboxylate or bibapcitide dicarboxylate. More preferably, the pharmaceutical composition of the invention comprises bibapcitide monocarboxylate and bibapcitide dicarboxylate. Most preferably, the pharmaceutical composition of the invention comprises bibapcitide monocarboxylate, bibapcitide dicarboxylate, and bibapcitide. The amounts of bibapcitide monocarboxylate, bibapcitide dicarboxylate, and bibapcitide in the pharmaceutical composition may vary in accordance with this embodiment of the invention. Commercially formulated bibapcitide, to be sold as ACUTECT™, typically contains between about 10% and about 50% bibapcitide monocarboxylate and between about 3% and about 12% bibapcitide dicarboxylate.

The pharmaceutical composition of the invention may further comprise a pharmaceutically acceptable diluent or a carrier such as species appropriate albumin. As used herein, a "pharmaceutically acceptable diluent or carrier" may include any and all solvents, dispersion media, antibacterial and antifungal agents, isotonic agents, enzyme inhibitors, and the like. The use of such media and agents for pharmaceutically active substances is well known in the art. For example, Sodium Chloride Injection and Ringer's Injection are commonly used as diluents. The precursor reagent is formulated as a sterile, pyrogen-free, parenterally acceptable aqueous solution which may optionally be supplied in lyophilized form and be reconstituted by the user. The preparation of such parenterally acceptable solutions, having due regard to pH, isotonicity, stability, and the like, is within the skill in the art.

The novel precursor reagents of the invention may be used to produce diagnostic or therapeutic agents derived from bibapcitide. Such agents include scintigraphic imaging agents for detecting and diagnosing thrombi, as described more fully in U.S. Pat. Nos. 5,508,020; 5,645,815; in U.S. Ser. No. 08/253,317 now U.S. Pat. No. 5,830,856 and in WO 93/23085; WO 93/25244; WO 94/23758; and WO 95/33496. Bibapcitide monocarboxylate and/or bibapcitide dicarboxylate may also be used to produce antithrombotic agents, as set forth in WO 94/07918. The precursor reagents of the invention may also be employed to produce an antithrombotic agent comprising a targeting peptide derived from bibapcitide which is covalently linked to a thrombolytic proteinase, as described in detail in copending applications U.S. Ser. No. 08/753,781 and U.S. Ser. No. 08/982,981.

When a precursor reagent of the invention is used to produce a labeled diagnostic or therapeutic agent derived from bibapcitide, any signal-generating label may be used. Such labels may be incorporated into or complexed with a precursor reagent of the invention in any manner appropriate for the particular label, either by direct covalent or noncovalent linkage with the precursor reagent or by indirect covalent or noncovalent linkage thereto. Suitable labels include radioactive labels, fluorescent labels, paramagnetic labels, heavy elements or rare earth ions suitable for use in computerized tomography, and the like. Radioactive labels are preferred. More preferably, γ-emitting radionuclides such as $^{123}I$, $^{67}Ga$, $^{111}In$, and $^{99m}Tc$, are used in the methods of the invention. Most preferably, $^{99m}Tc$ is used to label the precursor reagents of the invention. When $^{99m}Tc$ is used as a label, $^{99m}Tc$ is added to the pharmaceutical composition comprising bibapcitide monocarboxylate and/or bibapcitide dicarboxylate at a pH greater than about 5, and the resulting mixture is heated for a time and at a temperature sufficient to allow formation of apcitide monomer and radiolabeling of said monomer. Preferably, the mixture of the pharmaceutical composition comprising bibapcitide monocarboxylate and/or bibapcitide dicarboxylate and $^{99m}Tc$ is heated for about 15 minutes in a boiling water bath, to form a scintigraphic imaging agent comprising $^{99m}$Tc-labeled apcitide.

Labeled or unlabeled thrombus imaging or antithrombotic agents produced using the precursor reagents of the invention are preferably administered intravenously, in combination with a pharmaceutically acceptable carrier, to a living mammal. In accordance with the teachings of this invention, imaging or antithrombotic agents produced from pharmaceutical compositions comprising bibapcitide monocarboxylate and/or bibapcitide dicarboxylate are preferably administered in a single unit injectable dose, in any conventional medium for intravenous injection such as an aqueous saline medium, or in blood plasma medium. The amount of solution to be injected at unit dosage is from about 0.01 mL to about 10 mL.

Diagnostic and therapeutic agents produced from pharmaceutical compositions comprising bibapcitide monocarboxylate and/or bibapcitide dicarboxylate are preferably administered in a diagnostically or therapeutically effective amount to a mammal potentially at risk of a thrombus-related disease state or suffering from such a disease state.

As used herein, the term "diagnostically effective amount" means the total amount of each active component of the pharmaceutical composition of the diagnostic agent produced from bibapcitide monocarboxylate and/or bibapcitide dicarboxylate, or the total amount of such composition administered in a method employing the diagnostic agent, which is sufficient to produce a measurable signal localized at an in vivo thrombus site. As used herein, the term "therapeutically effective amount" means the total amount of each active component of the pharmaceutical composition of the therapeutic agent produced from bibapcitide monocarboxylate and/or bibapcitide dicarboxylate, or the total amount of such composition administered in a method employing the therapeutic agent, which is sufficient to show a meaningful patient benefit, i.e., reduction in the incidence and severity of thrombi as compared to that expected for a comparable group of patients not receiving the therapeutic agent, as determined by the attending physician. When applied to an individual active ingredient administered alone, the terms refer to that ingredient alone. When applied to a combination, the terms refer to combined amounts of the active ingredients that result in the diagnostic or therapeutic effect, whether administered in combination, serially, or simultaneously. For example, imaging agents or therapeutic agents produced from bibapcitide monocarboxylate and/or bibapcitide dicarboxylate may be administered at a dose of from about 0.1 to about 10 mg/kg body weight, administered intravenously either totally as a bolus or partly as a bolus followed by infusion over 1–2 hours. When radiolabeled diagnostic or therapeutic agents are produced from bibapcitide monocarboxylate and/or bibapcitide dicarboxylate, the unit dose to be administered has a radioactivity of about 0.01 mCi to about 100 mCi, preferably about 1 mCi to about 20 mCi. After intravenous administration, the thrombus site is monitored, in certain embodiments by radioimaging in vivo.

Methods for making bibapcitide monocarboxylate and bibapcitide dicarboxylate are more fully illustrated in the following examples, which are shown by way of illustration and not by way of limitation.

EXAMPLE 1

Synthesis of Bibapcitide Monocarboxylate

Bibapcitide trifluoroacetate (100 mg) was suspended in 10 mL of acetonitrile ($CH_3CN$), sonicated for one minute, and then diluted with 40 mL of water ($H_2O$). The peptide dissolved completely upon the addition of water ($H_2O$). To this solution were added 40 mL of 0.05 M sodium phosphate at pH 7 causing the solution to become slightly cloudy. The peptide solution was pH 7.2. The solution was incubated in a boiling water bath for three minutes which resulted in a clear solution. HPLC analysis indicated the presence of bibapcitide dicarboxylate, bibapcitide monocarboxylate, and bibapcitide in approximate amounts of 26%, 54%, and 14%, respectively. The reaction solution was loaded directly onto a 47×300 mm Delta-Pak C18 column equilibrated in 10 mM ammonium bicarbonate ($NH_4HCO_3$) adjusted to pH 6–6.5 with solid $CO_2$ (Mobile Phase C). The column was flushed with Mobile Phase C for five minutes followed by a gradient of 100/0 C/D to 90/10 C/D over five minutes, and then 90/10 C/D to 80/20 C/D over 30 minutes (Mobile Phase D=10 mM $NH_4HCO_3$ in 75/25 $CH_3CN/H_2O$ at pH 6–6.5). The HPLC buffers were continually maintained at pH 6–6.5 with solid $CO_2$. Fractions were collected based upon effluent monitoring at 220 nm. The fractions were then analyzed by analytical HPLC and those found to contain pure ($\geq 98\%$) bibapcitide monocarboxylate were pooled and lyophilized to afford approximately 30 mg of bibapcitide monocarboxylate (30% yield) as the ammonium carbonate salt, a white powder. NMR analysis of the bibapcitide monocarboxylate (20% $CD_3CN/80\%$ $H_2O$, pH 6, T=20° C.) so produced is set forth in Table 3 below.

TABLE 3

$^1$H NMR Chemical Shift Data (δ, ppm) for Bibapcitide Monocarboxylate

| Amino Acid | NH (amide) | α-CH | Other protons in Amino Acid | |
|---|---|---|---|---|
| D-Tyr$^1$ | 8.57 | 4.54 | 3.00 ($CH_2$) | 3.37, 3.43 (CO—$\underline{CH_2}$—S) |
| | | | | 6.85, 7.15 (aromatic) |
| Apc$^2$ | 8.45 | 4.49 | 2.81, 2.89 ($CH_2$) | 3.06 ($\underline{CH_2}$—$NH_2$) |
| | | | | 2.50 (—S—$\underline{CH_2}$) |
| | | | | 1.90 ($CH_2$—$\underline{CH_2}$—$CH_2$) |
| Gly$^3$ | 8.36 | 3.09, 4.90 | | |
| Asp$^4$ | 8.40 | 4.63 | 2.67 ($CH_2$) | |
| Cys$^5$ | 8.33 | 4.46 | 3.00, 3.08 | |
| Gly$^6$ | 8.41 | 4.00 | | |
| Gly$^7$ | 8.16 | 4.02 | | |
| Cys$^8$ | 8.30 | 4.61 | 2.95, 3.13 | |
| Gly$^9$ | 8.47 | 4.01 | | |
| Cys$^{10}$* | 8.25; 8.26 | 4.62; 4.64 | 2.93, 3.13; | |
| | | | 2.94, 3.14 | |

TABLE 3-continued

¹H NMR Chemical Shift Data (δ, ppm) for Bibapcitide Monocarboxylate

| Amino Acid | NH (amide) | α-CH | Other protons in Amino Acid |
|---|---|---|---|
| Acm[8,10] | 8.50 | 4.33 | 2.03 ($CH_3$) |
| Gly[11] | 8.50 | 3.99 | |
| Gly[12] | 8.23 | 4.01 | |
| Cys[13]* | 8.31; 8.54 | 4.65; 4.52 | 3.25; 3.05 |
| C-terminal amide | 7.65, 7.11; 7.60, 7.11; 7.64, 7.19 | | |
| 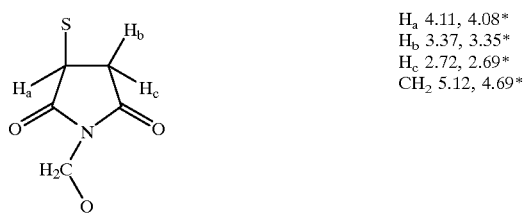 | | | $H_a$ 4.11, 4.08*<br>$H_b$ 3.37, 3.35*<br>$H_c$ 2.72, 2.69*<br>$CH_2$ 5.12, 4.69* |
| 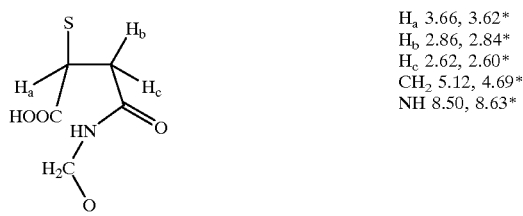 | | | $H_a$ 3.66, 3.62*<br>$H_b$ 2.86, 2.84*<br>$H_c$ 2.62, 2.60*<br>$CH_2$ 5.12, 4.69*<br>NH 8.50, 8.63* |

*Diastereomeric resonances

EXAMPLE 2

Synthesis of Bibapcitide Dicarboxylate

Bibapcitide trifluoroacetate (100 mg) was suspended in five mL of $CH_3CN$, sonicated for one minute, and then diluted with 25 mL of $H_2O$. The peptide dissolved completely upon the addition of $H_2O$. To this solution was added one mL of saturated sodium bicarbonate ($NaHCO_3$) and 0.5 mL of 1 M potassium carbonate ($K_2CO_3$). The peptide solution was estimated as pH 8.5 by pH paper. The solution became cloudy upon addition of $K_2CO_3$ but slowly cleared over two hours at room temperature. After three hours the reaction was found to contain 84% bibapcitide dicarboxylate as measured by analytical HPLC. The reaction solution was loaded directly onto a 47×300 mm Delta-Pak C18 column equilibrated in 10 mM ammonium bicarbonate ($NH_4HCO_3$) adjusted to pH 6–6.5 with solid $CO_2$ (Mobile Phase C). The column was flushed with 100% Mobile Phase C for 5 minutes followed by a gradient of 100/0 C/D to 90/10 C/D over five minutes, and then 90/10 C/D to 70/30 C/D over 30 minutes. The HPLC buffers were continually maintained at pH 6–6.5 with solid $CO_2$. Fractions were collected based upon effluent monitoring at 220 nm. The fractions were then analyzed by analytical HPLC and those found to contain pure (≧98%) bibapcitide dicarboxylate were pooled and lyophilized to yield approximately 54 mg of bibapcitide dicarboxylate (peptide content 86%, isolated yield 53%) as the ammonium carbonate salt, a white powder. NMR analysis of the bibapcitide dicarboxylate (20% $CD_3CN$/80% $H_2O$, pH 6, T=20° C.) so produced is set forth in Table 4 below.

TABLE 4

¹H NMR Chemical Shift Data (δ, ppm) for Bibapcitide Dicarboxylate

| Amino Acid | NH (amide) | α-CH | Other protons in Amino Acid | |
|---|---|---|---|---|
| D-Tyr[1] | 8.53 | 4.53 | 3.01 ($CH_2$) | 3.39, 3.42 (CO—$\underline{CH_2}$—S)<br>6.86, 7.17 (aromatic) |
| Apc[2] | 8.37 | 4.51 | 2.83, 2.91 ($CH_2$) | 3.06 ($\underline{CH_2}$—$NH_2$)<br>2.51 (—S—$\underline{CH_2}$)<br>1.92 ($CH_2$—$\underline{CH_2}$—$CH_2$) |
| Gly[3] | 8.34 | 3.88, 4.09 | | |
| Asp[4] | 8.37 | 4.66 | 2.75 ($CH_2$) | |
| Cys[5] | 8.30 | 4.45 | 3.00, 3.08 | |
| Gly[6] | 8.35 | 3.98 | | |
| Gly[7] | 8.10 | 4.01 | | |
| Cys[8] | 8.27 | 4.61 | 2.97, 3.14 | |
| Gly[9] | 8.41 | 4.00 | | |
| Cys[10] | 8.21 | 4.63 | 2.96, 3.14 | |
| Acm[8,10] | 8.45 | 4.33 | 2.03 ($CH_3$) | |

TABLE 4-continued

<sup>1</sup>H NMR Chemical Shift Data (δ, ppm) for Bibapcitide Dicarboxylate

| Amino Acid | NH (amide) | α-CH | Other protons in Amino Acid | |
|---|---|---|---|---|
| Gly[11] | 8.47 | 4.01 | | |
| Gly[12] | 8.18 | 4.00 | | |
| Cys[13]* | 8.30; 8.50 | 4.54; 4.53 | 3.15; 3.09 | |
| C-terminal amide* | 7.63, 7.05; 7.58, 7.05 | | | |
| [structure 1] | | | $H_a$ 3.70, 3.67* <br> $H_b$ 2.86, 2.85* <br> $H_c$ 2.63, 2.62* <br> $CH_2$ 4.68 <br> NH 8.54 | Major hydrolysis product (>80% by NMR) |
| [structure 2] | | | $H_a$ 3.78, 3.75* <br> $H_b$ 2.89, 2.88* <br> $H_c$ 2.69, 2.67* <br> $CH_2$ 4.73, 4.72* <br> NH 8.80, 8.74* | Minor hydrolysis product (<20% by NMR) |

*Diastereomeric resonances

It should be understood that the foregoing disclosure emphasizes certain specific embodiments of the invention and that all modifications or equivalents thereto are within the spirit and scope of the invention as set forth in the appended claims.

What is claimed is:

1. A precursor reagent comprising bibapcitide monocarboxylate.

2. A precursor reagent comprising bibapcitide dicarboxylate.

3. A composition comprising bibapcitide monocarboxylate.

4. The composition of claim 3, further comprising bibapcitide dicarboxylate.

5. The composition of claim 4, further comprising bibapcitide.

6. A composition comprising bibapcitide dicarboxylate.

7. A pharmaceutical composition comprising bibapcitide monocarboxylate and a pharmaceutically acceptable carrier.

8. The pharmaceutical composition of claim 7, further comprising bibapcitide dicarboxylate.

9. The pharmaceutical composition of claim 8, further comprising bibapcitide.

10. A pharmaceutical composition comprising bibapcitide dicarboxylate and a pharmaceutically acceptable carrier.

* * * * *